United States Patent [19]

Vorbruggen

[11] 4,209,613

[45] Jun. 24, 1980

[54] PROCESS FOR THE PREPARATION OF NUCLEOSIDES

[75] Inventor: Helmut Vorbruggen, Berlin, Fed. Rep. of Germany

[73] Assignee: Schering Aktiengesellschaft, Berlin and Bergkamen, Fed. Rep. of Germany

[21] Appl. No.: 971,583

[22] Filed: Dec. 20, 1978

[30] Foreign Application Priority Data

Dec. 20, 1977 [DE] Fed. Rep. of Germany ....... 2757365

[51] Int. Cl.² ............................................. C07H 17/00
[52] U.S. Cl. ........................................ 536/23; 536/24
[58] Field of Search .............................. 536/24, 26, 23

[56] References Cited

U.S. PATENT DOCUMENTS

| | | | |
|---|---|---|---|
| 3,352,849 | 11/1967 | Shen et al. | 536/23 |
| 3,354,160 | 11/1967 | Duschinsky et al. | 536/23 |
| 3,531,464 | 9/1970 | Ryan et al. | 536/23 |
| 3,708,469 | 1/1973 | Vorbruggen et al. | 536/23 |
| 3,748,320 | 7/1973 | Vorbruggen et al. | 536/23 |
| 3,817,980 | 6/1974 | Vorbruggen et al. | 536/23 |
| 4,082,911 | 4/1978 | Vorbruggen | 536/26 |

OTHER PUBLICATIONS

Wittenburg, E., Chem. Ber. 101, 1095–1114 (1968).
Wittenburg, E., Z. Chem. 4, Jg. (1964), Hept8,303.

*Primary Examiner*—Johnnie R. Brown
*Assistant Examiner*—Blondel Hazel
*Attorney, Agent, or Firm*—Millen & White

[57] ABSTRACT

In a process for preparing a nucleoside by silylating the corresponding nucleoside base and reacting the silylated base with a 1-O-acyl, 1-O-alkyl, or 1-halogen derivative of a blocked monosaccharide or oligosaccharide in the presence of a catalyst, an improvement comprises silylating the base and reacting the sugar derivative in a single step.

11 Claims, No Drawings

PROCESS FOR THE PREPARATION OF NUCLEOSIDES

BACKGROUND OF THE INVENTION

In the conventional syntheses of nucleosides using the silyl method, as described, for example in U.S. Pat. No. 3,748,320 (German Pat. No. 1,919,307) or in U.S. Pat. No. 4,082,911 (DOS No. 2,508,312), it has been universally considered absolutely necessary to silylate the nucleoside bases, especially the pyrimidine bases, such as uracil, 2-thiouracil, cytosine, etc., as well as the purine bases such as adenine, $N^6$-benzoyladenine, hypoxanthine, xanthine and guanine, prior to the actual nucleoside synthesis. Only thereafter are the thus-formed, moisture-sensitive persilylated nucleoside bases reacted in a second reaction step with blocked 1-halogen sugars, 1-O-alkyl sugars and especially 1-O-acyl sugars in the presence of Friedel-Crafts catalysts, such as $SnCl_4$, $TiCl_4$, $ZnCl_2$, $BF_3$-etherate, $AlCl_3$, $SbCl_5$, or trimethylsilyl perfluoro alkyl sulfonates and/or $(CH_3)_3SiClO_4$.

The reaction of silylated bases with blocked sugars to form nucleosides is also known from U.S. patent application Ser. No. 670,741, filed Mar. 26, 1976, now allowed and U.S. Pat. Nos. 3,708,469, 3,891,623, 3,983,104 and 4,090,021.

The need to separately silylate the nucleoside base has led to disadvantages such as lower yields of end product nucleoside and, of course, the attendant time and expense associated with the extra separate step.

SUMMARY OF THE INVENTION

Accordingly, it is an object of this invention to provide an improved process of preparing nucleosides from nucleoside bases which are silylated by eliminating the conventional separate silylation step.

Upon further study of the specification and appended claims, further objects and advantages of this invention will become apparent to those skilled in the art.

These objects have been attained by providing in a process for preparing a nucleoside by silylating the corresponding nucleoside base and reacting the silylated base with a 1-O-acyl, 1-O-alkyl, or 1-halogen derivative of a blocked monosaccharide or oligosaccharide in the presence of a catalyst, the improvement which comprises silylating the base and reaching the sugar derivative in a single step. Additionally, in the same step, the silylatiion of the perfluoroalkenesulfonic acid, perchloric acid or fluoboric acid, and/or of the salts of these acids, to obtain the Friedel-Crafts catalyst, may also be effected.

DETAILED DISCUSSION

It has now been found that both reaction steps, i.e., the persilylation of the nucleoside bases and the subsequent nucleoside synthesis with the blocked sugar derivatives in the presence of Friedel-Crafts catalysts can, using appropriate amounts of the silylating reagent, be surprisingly combined into one step. Thus, the heretofore customary separate silylation of the nucleoside base can be omitted. Additionally, the separate silylation of perfluoroalkanesulfonic acids, perchloric acid or fluoboric acid, and/or of the salts of these acids, to obtain the Friedel-Crafts catalysts, as disclosed in U.S. Pat. No. 4,082,911, can likewise be omitted.

Accordingly, this invention relates to a process for the preparation of nucleosides by reacting the corresponding nucleoside bases with a 1-O-acyl, 1-O-alkyl, or 1-halogen derivative of a blocked, monomeric or oligomeric sugar in the presence of a catalyst, wherein the silylation of the base and the reaction with the sugar derivative are conducted simultaneously in a single step. For the silylation of the base, for each hydroxy, mercapto and amino group, a mixture of about 0.66 equivalent of hexamethyldisilazane (HMDS) and about 0.33 equivalent of trimethylhalosilane (with chlorine and bromine as the halogen), preferably trimethylchlorosilane (TCS), is preferably employed. Suitable catalysts include typical Friedel-Crafts catalysts, such as $SnCl_4$, $TiCl_4$, $ZnCl_2$, $BF_3$-etherate, $AlCl_3$ and $SbCl_5$. There can also be used trimethylsilyl perchlorate $(CH_3)_3SiClO_4$, $(CH_3)_3SiSO_3C_nF_{2n+1}$ wherein n is 1–10, preferably n is 1–4, and/or $(CH_3)_3SiBF_4$ (unstable according to published data by Evers in J. Inorg. Chem. 13:239 [1960]). These latter are produced in situ from the free acids and/or the salts thereof, especially the alkali metal salts, sodium and potassium being preferred, or ammonium salts, using a silylating agent, preferably an excess of the silylating agent used in silylating the base, especially trimethylchlorosilane (TCS).

All nucleoside organic bases are usable in the process of this invention. These are generally known to those skilled in the art and are disclosed, e.g., in the references mentioned above in the BACKGROUND OF THE INVENTION section of this application, whose disclosures are incorporated by reference herein for all details of the process of this invention, which are not otherwise specified herein, especially the disclosures of U.S. Pat. Nos. 3,748,320 and 4,082,911. For example, suitable such bases include

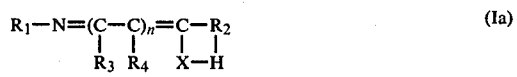

(Ia)

or

(Ib)

wherein

X is O or S;

n is 0 or 1;

$R_1$ and $R_2$ individually represent any desired saturated or unsaturated, optionally substituted organic residue or together represent a bivalent organic residue which can contain one or two nitrogen atoms; and $R_3$ and $R_4$ individually represent hydrogen, alkyl, alkoxycarbonyl, alkylaminocarbonyl or together represent the residues

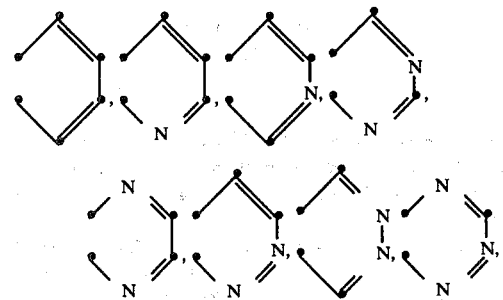

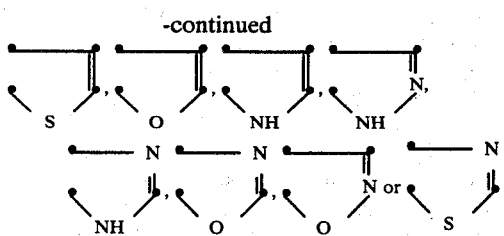

which can be conventionally substituted. It is preferred that the alkyl portions of these $R_2$ and $R_4$ groups be lower alkyl moieties. Throughout this specification, "lower" refers to 1–4 C atoms.

When $R_1$ and $R_2$ represent an organic residue, such residue is particularly a lower alkyl group, preferably of 1–4 carbon atoms. Examples are methyl, ethyl, propyl and butyl. Also, $C_{6-10}$-aryl or $C_{6-10}$-ar-$C_{1-4}$-alkyl groups can be used, as $R_1$ and/or $R_2$, e.g., phenyl, benzyl, tolyl, xylyl, etc. Other organic residues are equivalent to these preferred ones as mentioned above as long as they are compatible with the process of this invention.

The nature of the bivalent residues for $R_1$ and $R_2$, as well as for $R_3$ and $R_4$, as can be seen from the generic definitions thereof, is not critical as long as it is compatible with the process of this invention. Thus, those equivalent such residues are the corresponding ones which contain, for example, the following substituents: lower alkyl, trifluoromethyl, acyl, hydroxy, alkoxy, acyloxy, carboxy, carboxamido, alkoxycarbonyl, dialkylaminocarbonyl, amino, nitro, nitriloxo or halogen. Each alkyl moiety mentioned is preferably a lower alkyl moiety.

Preferred starting compounds are nucleoside organic bases wherein $R_1$ and $R_2$ are linked to a ring, especially in such a way that the heterocyclic base contains five or six atoms, among which are one to three nitrogen atoms, in the ring.

The organic bases according to Formulae Ia and Ib are thus derived preferably from the following heterocyclic bases: uracil, cytosine, 6-azauracil, 2-thio-6-azauracil, thymine, N-acyl-adenine, guanine, lumazine, imidazole, pyrazine, thiazole and triazole, which can optionally be substituted by one or more of the above-mentioned residues $R_1$, $R_2$, as well as $R_3$ and $R_4$.

When $R_1$ and $R_2$ are linked to each other in a ring, the bivalent residue $R_1$, $R_2$ represents, in particular:

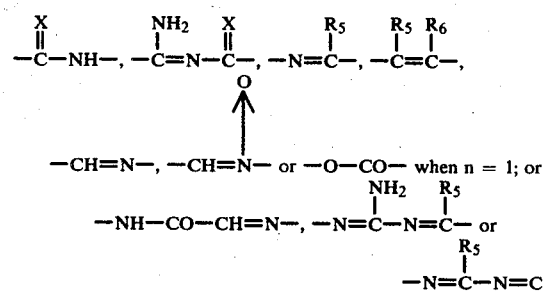

when n=0, wherein X is as defined above and $R_5$ and $R_6$ individually are hydrogen, alkyl, alkoxycarbonyl or alkylaminocarbonyl, preferably containing lower alkyl moieties.

The sugar derivatives used in the process of this invention are preferably derived from ribose, deoxyribose, arabinose, and glucose, or from 2-substituted derivatives of tetrahydrofuran or tetrahydropyran. In addition, also usable are peracylated oligomers of sugars, especially of glucose, such as, for example, peracetylated cellobiose, cellotriose and/or polymers of 10–50 glucose units.

Suitably all free hydroxy groups of the sugars are blocked during the process. Suitable sugar blocking groups are fully conventional and non-critical and include the blocking groups conventional in sugar chemistry, such as, for example, the acyl, benzoyl, p-chlorobenzoyl, p-nitrobenzoyl, p-toluyl, and benzyl groups.

In the nucleosides obtained by this process, the free or blocked sugar residue is preferably linked to the nitrogen atom in the manner of a $\beta$-glycoside.

When the process of this invention is used to prepare nucleosides which contain O-acyl-blocked sugar residues, then the acyl groups of the following specified acids are furthermore particularly suitable, inter alia, in addition to the specific blocking groups mentioned hereinabove: propionic acid, butyric acid, valeric acid, caproic acid, enanthic acid, undecylic acid, oleic acid, pivalic acid, cyclopentylpropionic acid, phenylacetic acid and adamantanecarboxylic acid.

Details of typical 1-O acyl, 1-O-alkyl or 1-halogen derivatives of sugars which can be used in the process of this invention are found in the references cited in the BACKGROUND OF THE INVENTION section and are fully conventional. See also Synthetic Procedure in Nucleic Acid Chemistry Vol. 1, Editors W. W. Zorbach and R. S. Tipson, Interscience Publishers, New York 1968.

The process of this invention is generally applicable to the preparation of nucleosides. Preferred products of the process are nucleosides of Formula II

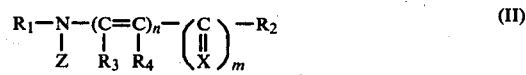

wherein
$R_1$, $R_2$, $R_3$, $R_4$, X and n are as defined above;
Z is a free or blocked sugar residue; and
m is 0 or 1.

The nucleosides producible according to this process, and especially the process products of Formula II, are biologically active. Due to their specific solubility, they can be administered, depending on the choice of substituent, for example, either systemically as an aqueous or alcoholic solution, or locally as an ointment or jelly.

The use and administration of these products as pharmaceuticals is fully conventional. See, for example, the disclosures in the U.S. patents mentioned in the BACKGROUND section of this application, which are incorporated by reference herein, especially U.S. Pat. No. 3,748,320.

The compounds produced—depending, of course, on the starting compound—exhibit, for example, enzyme-inhibiting, antibacterial, antiviral, cytostatic, antipsoriatic and/or anti-inflammatory activities.

The reaction of the nucleoside organic bases, e.g., the bases of Formula Ia or Ib, with a 1-O-acyl, 1-O-alkyl, or 1-halogen derivative of a blocked sugar in the presence of the silylating agent and Friedel-Crafts catalyst and/or in the presence of the chemicals necessary for an in situ formation of this catalyst takes place in an inert organic solvent. Suitable such solvents include, for example, ethylene, ethylene chloride, chloroform, acetonitrile, benzene, toluene, dioxane, tetrahydrofuran, dimethylformamide, carbon disulfide, chlorobenzene, sulfolane, or molten dimethylsulfone. Preferred solvents are acetonitrile, ethylene chloride and chloroform.

The reaction can be conducted at room temperature or at higher or lower temperatures, preferably at 0°–100° C. The reactants are generally used in the reaction in approximately equimolar amounts, but the heterocyclic base is frequently employed in a minor excess to obtain a maximally quantitative conversion of the sugar component. The catalyst is used preferably in a molar excess, e.g., 1.2–2.4 equivalents.

For the in situ silylation of the heterocyclic bases, it is necessary to utilize for each hydroxy, mercapto and amino group in these bases at least one, e.g. 1.05–1.5, equivalents of silylating agent, e.g., one equivalent of trimethylchlorosilane (TCS) or, preferably, a mixture of 0.66 equivalent of hexamethyldisilazane (HMDS) and 0.33 equivalent of TCS, leading to the production of only 0.33 equivalent on $NH_4Cl$. Other suitable silylating agents are fully conventional and are disclosed in Chemistry and Industry, 794 (1978) whose disclosure is incorporated by reference herein.

When it is desired to effect the in situ formation of the catalytic trimethylsilyl esters of perfluoroalkanesulfonic acids, perchloric acid, and/or fluoboric acid from the corresponding acids or salts, additional, at least equivalent amounts, e.g., 1–2 equivalents, of silylating agent, e.g., preferably trimethylchlorosilane (TCS) or trimethylbromosilane (TBS), must be added to the reaction mixture in order to silylate the free acids or the salts thereof. Equivalent catalysts whose silyl esters may be formed in situ are those other mineral acids or strong organic acids which have been conventionally employed in the process of this invention.

The catalysts suitable for use in this novel process are the same as the catalysts which are conventionally employed in the basic reaction. However, when, for example, the catalyst is a free perfluoroalkanesulfonic acid or a salt thereof and/or the salt of a perchloric acid, it may be provided solely in situ as described above, in accordance with the following formulae, with the formation of HCl or HBr and/or sodium chloride, potassium chloride or ammonium chloride.

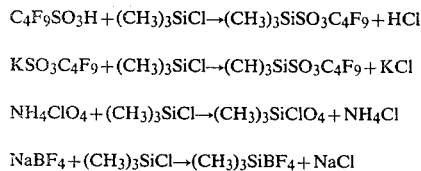

Suitable such free acids are anhydrous perfluoroalkanesulfonic acids, especially trifluoromethanesulfonic acid and perfluorobutanesulfonic acid, perchloric acid, as well as fluoboric acid and the salts thereof, e.g., the ammonium, sodium, and potassium salts. The alkane moiety is preferably lower alkane.

The yields of this novel, one-stage nucleoside synthesis, wherein the β-anomers of the nucleosides are formed predominantly and/or exclusively, are higher than those of the conventional processes, considering the losses incurred in the previously customary, separate silylation of the organic base. Times of reaction generally are 0.5–30 hours. It is preferred that the reaction medium be agitated during the course of the process and, of course, an inert atmosphere, such as argon, nitrogen, etc. can be employed.

The order of addition of the components of the reaction is not critical but it is preferred that trimethylchlorosilane (TCS) is added as the last component over a short time.

To produce the desired compounds having free hydroxy groups, the blocking groups can be removed in the usual way; for example, by treatment in alcoholic solutions of ammonia or alcoholates, aqueous or alcoholic alkali, as well as for the benzyl ethers, by reduction or hydrogenation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

0.56 g (5 millimoles) of uracil, 2.52 g. (5 mmol) of 1-O-acetyl-2,3,5-tri-O-benzoyl-β-D-ribofuranose, as well as 4.06 g. (12 mmol) of potassium salt of perfluorobutanesulfonic acid were suspended in 70 ml. of absolute acetonitrile; under agitation and argon, 0.74 ml. (3.5 mmol) of hexamethyldisilazane (HMDS) and 1.89 ml. (15 mmol) of trimethylchlorosilane (TCS) were added, and the mixture was refluxed for 14 hours. After dilution with methylene chloride the mixture was extracted with saturated $NaHCO_3$ solution, and the methylene chloride phase was washed with water. After drying ($Na_2SO_4$) and evaporation, the brown foam (3.19 g.) was crystallized from 95% ethanol, yielding in several portions 1.87 g. of pure uridine 2',3',5'-tri-O-benzoate. After chromatographing the mother liquor on silica gel and elution with toluene-ethyl acetate (8:2), another 0.45 g., in total 2.32 g.=83.5% of pure uridine 2',3',5'-tri-O-benzoate was obtained.

EXAMPLE 2

1.12 g. (10 mmol) of uracil, 5.04 g. (10 mmol) of 1-O-acetyl-2,3,5-tri-O-benzoyl-β-D-ribofuranose and 1.8 g. (12 mmol) of trifluoromethanesulfonic acid were combined 100 ml. of absolute acetonitrile with 1.8 g.=2.3 ml. (12 mmol) of hexamethyldisilazane (HMDS) and 1.3 g. (12 mmol) of trimethylchlorosilane (TCS); the mixture was stirred for 4 hours at 24° C. and then refluxed for 1½ hours. After the mixture had been worked up as described in Example 1, 4.50 g.=81% of crystalline uridine 2',3',5'-tribenzoate was otained.

EXAMPLE 3

0.56 g. (5 mmol) of uracil, 2.52 g. (5 mmol) of 1-O-acetyl-2,3,5-tri-O-benzoyl-β-D-ribofuranose were agitated in 75 ml. of absolute acetonitrile with 0.65 g. (4 mmol) of HMDS, 0.43 g. (4 mmol) of TCS, and 1.56 g. (6 mmol) of $SnCl_4$ for 2 hours at 24° C. The mixture was worked up as set forth in Example 1, yielding 83.1% of crystalline uridine tribenzoate.

EXAMPLE 4

0.56 g. (5 mmol) of uracil was agitated in 70 ml. of absolute acetonitrile with 1.86 g. (3.5 mmol) of HMDS and 2.55 g. (15.5 mmol) of TCS, as well as 1.69 g. (12 mmol) of NaClO$_4$·H$_2$O for 30 minutes at 24° C. The reaction mixture was then combined with 2.52 g. (5 mmol) of 1-O-acetyl-2,3,5-tri-O-benzoyl-β-D-ribofuranose and refluxed for 20 hours. The mixture was worked up as described in Example 1, yielding 58% of crystalline uridine tribenzoate.

EXAMPLE 5

0.56 g. (5 mmol) of uracil, 2.52 g. (5 mmol) of 1-O-acetyl-2,3,5-tri-O-benzoyl-β-D-ribofuranose were refluxed in 70 ml. of absolute acetonitrile with 1.41 g. (12 mmol) of NH$_4$ClO$_4$, 0.57 g. (3.5 mmol) of HMDS, and 1.68 g. (15.5 mmol) of TCS for 20 hours. The mixture was worked up as set forth in Example 1, thus producing 40% of crystalline uridine tribenzoate.

EXAMPLE 6

0.56 g. (5 mmol) of uracil, 2.52 g. (5 mmol) of 1-O-acetyl-2,3,5-tri-O-benzoyl-β-D-ribofuranose were refluxed in 70 ml. of absolute acetonitrile with 1.32 g. (12 mmol) of NaBF$_4$, 0.57 g. (3.5 mmol) of HMDS, and 1.68 g. (15.5 mmol) of TCS for 2 hours. The mixture was worked up as set forth in Example 1, yielding 43% of crystalline uridine tribenzoate.

EXAMPLE 7

0.64 g. (5 mmol) of 2-thiouracil, 2.52 g. (5 mmol) of 1-O-acetyl-2,3,5-tri-O-benzoyl-β-D-ribofuranose, 4.06 g. (12 mmol) of the potassium salt of perfluorobutanesulfonic acid were refluxed in 70 ml. of absolute acetonitrile with 0.57 g. (3.5 mmol) of HMDS, as well as with 1.68 g. (15.5 mmol) of TCS for 17 hours and then worked up as described in Example 1. Yield: 1.37 g. (47.74%) of crystalline 2-thiouridine tribenzoate, m.p. 105°–106° C.

EXAMPLE 8

0.64 g. (5 mmol) of 2-thiouracil, 2.52 g. (5 mmol) of 1-O-acetyl-2,3,5-tri-O-benzoyl-β-D-ribofuranose were combined in 75 ml. of absolute acetonitrile with 0.65 g. (4 mmol) of HMDS, 0,43 g. (4 mmol) of TCS, and 1.56 g. (6 mmol) of SnCl$_4$ and after 7 hours at 24° C. the mixture was worked up as set forth in Example 1, thus obtaining 64% of crystalline 2-thiouridine tribenzoate.

EXAMPLE 9

0.63 g. (5 mmol) of 5-methoxyuracil, 2.52 g. (5 mmol) of 1-O-acetyl-2,3,5-tri-O-benzoyl-β-D-ribofuranose and 4.06 g. (12 mmol) of the potassium salt of perfluorobutanesulfonic acid were refluxed in 70 ml. of absolute acetonitrile with 0.57 g. (3.5 mmol) of HMDS, 1.63 g. (15 mmol) of TCS for 20 hours and worked up as described in Example 1. Crystallization of the crude product from ethyl acetate-hexane yielded 2.09 g. (71.4%) of crystalline 5-methoxyuridine 2',3',5'-tri-O-benzoate.

EXAMPLE 10

0.55 g. (5 mmol) of cytosine, 2.52 g. (5 mmol) of 1-O-acetyl-2,3,5-tri-O-benzoyl-β-D-ribofuranose and 4.06 g. (12 mmol) of the potassium salt of perfluorobutanesulfonic acid were refluxed in 70 ml. of absolute acetonitrile with 0.57 g. (3.5 mmol) of HMDS, 1.68 g. (15.5 mmol) of TCS for 27 hours, worked up as usual, and chromatographed with toluene-ethyl acetate (3:2) on silica gel, thus obtaining 1.55 g. (56%) of amorphous cytidine 2',3',5'-tribenzoate.

EXAMPLE 11

0.21 g. (1.5 mmol) of 2-thio-5-methyluracil, 8.73 g. of peracetylcellopentacosanose, 1.22 g. of the potassium salt of perfluorobutanesulfonic acid were refluxed with 0.17 g. (1.05 mmol) of HMDS, 0.51 g. (4.65 mmol) of TCS for 13 hours in 70 ml. of absolute acetonitrile, and then worked up as usual (emulsions). The residue was saponified with 200 ml. of methanolic NH$_3$ for 3 days at 24° C., evaporated, extracted with ether, and then extracted three times with methanol-H$_2$O (1:1) and washed with methanol. The slightly greyish residue showed, in the nitrogen analysis, a nitrogen content of 1.25%.

EXAMPLE 12

0.64 g. (5 mmol) of 2-thiouracil, 1.95 g. (5 mmol) of β-pentaacetylglucose in 75 ml. of absolute acetonitrile were refluxed for 2 hours with 0.65 g. (4 mmol) of HMDS, 0.43 g. (4 mmol) of TCS, as well as 1.56 g. (6 mmol) of SnCl$_4$, worked up as set forth in Example 1, and chromatographed on silica gel with toluene-ethyl acetate (7:3), thus obtaining 57% of 1-(2,3,4,6-tetraacetyl-β-D-glucopyranosyl)-2-thiouracil.

EXAMPLE 13

0.47 g. (5 mmol) of 4-pyridone, 2.52 g. (5 mmol) of 1-O-acetyl-2,3,5-tri-O-benzoyl-β-D-ribofuranose, and 4.06 g. (12 mmol) of the potassium salt of perfluorobutanesulfonic acid were refluxed with 0.29 g. (1.75 mmol) of HMDS and 1.49 g. (13.75 mmol) of TCS in 70 ml. of absolute acetonitrile for 12 hours. The usual working-up step (Example 1) yielded after chromatography on silica gel with ethyl acetate-methanol (95:5) 65% of amorphous 1-(2',3',5'-tri-O-benzoyl-β-D-ribofuranosyl)-4-pyridone.

EXAMPLE 14

1.19 g. (5 mmol) of N$^6$-benzoyladenine, 2.52 g. (5 mmol) of 1-O-acetyl-2,3,5-tri-O-benzoyl-β-D-ribofuranose, and 4.06 g. (12 mmol) of the potassium salt of perfluorobutanesulfonic acid were refluxed with 0.57 g. (3.5 mmol) of HMDS and 1.68 g. (15.5 mmol) of TCS in 70 ml. of absolute acetonitrile for 21 hours and then worked up as described in Example 1. The crude product (3.9 g.) was allowed to stand in 100 ml. of methanolic NH$_3$ for 4 days at 24° C., evaporated, and the residue recrystallized from a small amount of water after extraction eith ether, thus obtaining 0.84 g. (63%) of pure, crystalline adenosine.

EXAMPLE 15

0.56 g. (5 mmol) of uracil was agitated in 50 ml. of absolute ethylene chloride with 0.65 g. (4 mmol) of HMDS, 0.43 g. (4 mmol) of TCS, and 1.56 g. (0.71 ml.=6 mmol) of SnCl$_4$ for one hour; then the reaction mixture was combined with 2.52 g. (5 mmol) of 1-O-acetyl-2,3,5-tri-O-benzoyl-β-D-ribofuranose, and the mixture was stirred for another 2 hours. After working up the mixture as usual, 73% of crystalline uridine 2',3',5'-tri-O-benzoate was obtained.

EXAMPLE 16

0.65 g. (5 mmol) of 5-fluorouracil was agitated in 50 ml. of absolute ethylene chloride for one hour with 0.65 g. (4 mmol) of HMDS, 0.43 g. (4 mmol) of TCS, and 1.56 g. (6 mmol) of SnCl$_4$; then 0.65 g. (5 mmol) of 2-acetoxytetrahydrofuran or 0.51 g. (5 mmol) of 2- methoxytetrahydrofuran was added to the mixture, and the latter was agitated for 2 hours and 4 hours, respectively, at 24° C. The mixture was worked up as described in Example 1, giving in an 87% yield N$_1$-(2-tetrahydrofuryl)-5-fluorouracil, m.p. 165°–167° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing a nucleoside by silylating the corresponding nucleoside base and reacting the silylated base with a 1-O-acyl, 1-O-alkyl or 1-halogen derivative of a blocked monosaccharide or oligosaccharide in the presence of a catalyst, the improvement which comprises silylating the base and reacting the sugar derivative in a single step.

2. The process of claim 1, wherein the catalyst is a Friedel-Crafts catalyst selected from SnCl$_4$, TiCl$_4$, ZnCl$_2$, BF$_3$-etherate, AlCl$_3$ and SbCl$_5$.

3. The process of claim 1, wherein the catalyst is a trialkylsilyl ester of a perfluoroalkanesulfonic acid, perchloric acid or fluoboric acid or an alkali metal or ammonium salt thereof.

4. The process of claim 3, wherein the catalytic trialkysilyl ester is simultaneously formed during the reaction of the base and the sugar derivative by reacting the corresponding free acid or salt thereof with a silylating agent.

5. The process of claim 1, wherein the silylating agent is trimethylhalosilane or hexamethyldisilazane.

6. The process of claim 5, wherein the silylating agent is an amount of a mixture of trimethylchlorosilane and hexamethyldisilazane equivalent to the amount of nucleoside base used.

7. The process of claim 6, wherein the catalyst is (CH$_3$)$_3$SiBF$_4$, (CH$_3$)$_3$SiClO$_4$ or (CH$_3$)$_3$SiSO$_3$C$_n$F$_{2n+1}$, wherein n is 1–10, and is formed during the course of the reaction by reaction of the corresponding free acid or a salt thereof with an amount of trimethylchlorisilane additional to that added to react with the nucleoside base.

8. The process of claim 1, wherein the starting nucleoside is an organic base of the formula

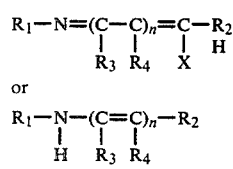

wherein
n is 0 or 1;
X is O or S;
R$_1$ and R$_2$ individually are lower alkyl, C$_{6-10}$ aryl or C$_{6-10}$-ar-C$_{1-4}$ or together form a bivalent residue of the formula

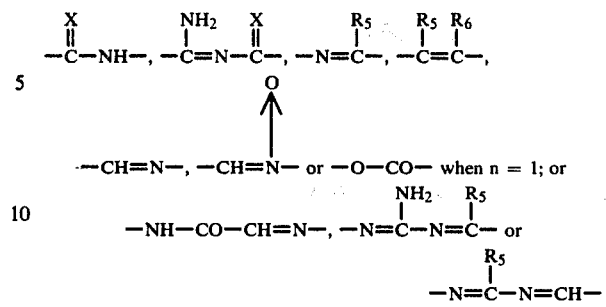

when n=0 wherein R$_5$ and R$_6$ and R$_3$ and R$_4$ all individually are hydrogen, lower alkyl, lower alkoxycarbonyl or lower alkylaminocarbonyl, or R$_3$ and R$_4$ together represent a bivalent residue of the formula:

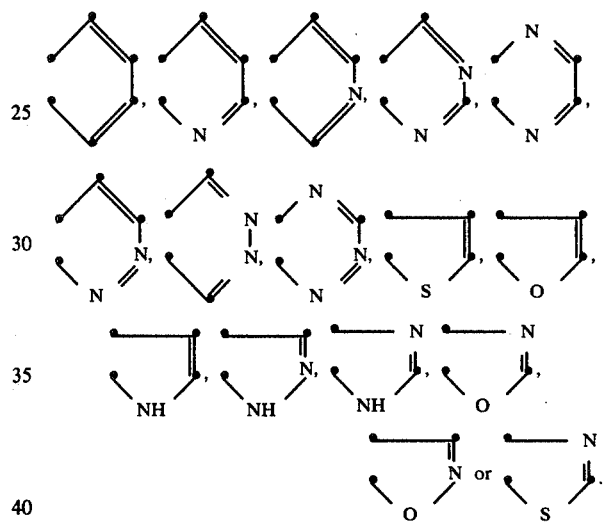

9. The process of claim 8 wherein the organic base is a heterocyclic base.

10. The process of claim 8, wherein the starting material is an organic base of the formula

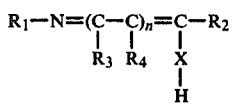

wherein
n is 1; and
R$_1$ and R$_2$ together represent

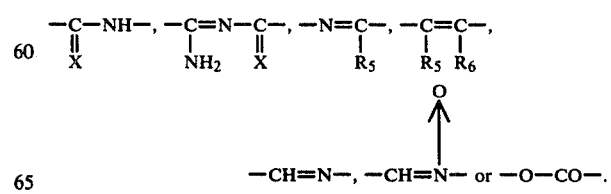

11. The process of claim 8, wherein the starting material is an organic base of the formula

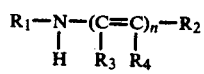
wherein
 n is 0; and
 $R_1$ and $R_2$ together represent
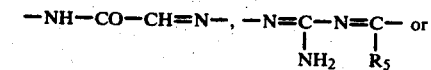
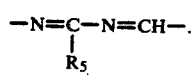
* * * * *